United States Patent [19]

Hamprecht et al.

[11] Patent Number: 5,237,063
[45] Date of Patent: Aug. 17, 1993

[54] TRIFLUORO- AND CHLORODIFLUOROMETHOXYPYRIMIDINES AND THE PREPARATION THEREOF

[75] Inventors: Gerhard Hamprecht, Weinheim; Hans-Josef Wolf, Maxdorf, both of Fed. Rep. of Germany

[73] Assignee: BASF Aktiengesellschaft, Ludwigshafen, Fed. Rep. of Germany

[21] Appl. No.: 663,342

[22] Filed: Mar. 4, 1991

[30] Foreign Application Priority Data

Mar. 8, 1990 [DE] Fed. Rep. of Germany ....... 4007317

[51] Int. Cl.$^5$ ................. C07D 239/34; C07D 239/52; C07D 239/60
[52] U.S. Cl. .................. 544/303; 544/313; 544/319; 504/214
[58] Field of Search .......... 544/319, 303, 313; 514/269, 274

[56] References Cited

U.S. PATENT DOCUMENTS

| | | | |
|---|---|---|---|
| 4,352,806 | 10/1982 | Katz et al. | 424/251 |
| 4,443,243 | 4/1984 | Fory et al. | 71/93 |
| 4,826,528 | 5/1989 | Mengel et al. | 71/92 |
| 4,849,009 | 7/1989 | Zondler | 71/92 |
| 4,875,923 | 10/1989 | Schurter et al. | 71/92 |
| 4,877,446 | 10/1989 | Elbe | 71/92 |
| 4,900,827 | 2/1990 | Seifert et al. | 544/303 |

OTHER PUBLICATIONS

Pein et al, Tetrahedron Letters, vol. 26(40) pp. 4915–4918 (1985).

*Primary Examiner*—Mukund J. Shah
*Assistant Examiner*—Matthew V. Grumbling
*Attorney, Agent, or Firm*—Keil & Weinkauf

[57] ABSTRACT

Substituted trifluoro- and chlorodifluoromethoxypyrimidines of the formula I

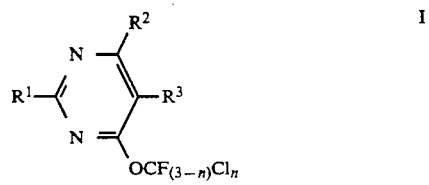

where $R^1$, $R^2$ and $R^3$ are each, independently of one another, hydrogen, halogen or haloalkyl, and $R^1$ and/or $R^2$ are also trifluoromethoxy or chlorodifluoromethoxy, and n is 0 or 1, are prepared as described.

9 Claims, No Drawings

TRIFLUORO- AND CHLORODIFLUOROMETHOXYPYRIMIDINES AND THE PREPARATION THEREOF

The present invention relates to novel substituted trifluoro- and chlorodifluoromethoxypyrimidines of the formula I

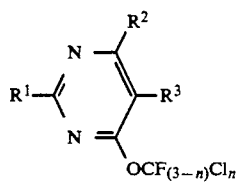

where $R^1$, $R^2$ and $R^3$ are each, independently of one another, hydrogen, halogen or haloalkyl, and $R^1$ and/or $R^2$ are also trifluoromethoxy or chlorodifluoromethoxy, and n is 0 or 1, and a process for preparing them by halogen replacement in 4-trichloromethoxypyrimidines.

The present invention also relates to the compounds II and a process for the preparation thereof.

The compounds I and II are used as intermediates for preparing organic compounds, and especially for preparing herbicidal sulfonylureas.

Because of the difficulty of handling fluorine, which is extremely reactive, non-selective and toxic, to date no methods for the direct fluorination of alkoxypyrimidines have been disclosed. Trifluoro- and chlorodifluoromethoxypyrimidines have not been disclosed either. Difluoromethoxypyrimidines have been obtained by a circuitous route, for example by ester cleavage of 2-amino-4,6-dimethoxypyrimidine to give the corresponding 4-hydroxy compound and subsequent reaction with chlorodifluoromethane to give 2-amino-4-difluoromethoxy-6-methoxypyrimidine in 10% yield (EP-A-70,804, Example 6). Since the starting material is prepared from trichloropyrimidine by reaction with ammonia and methanol, and then the methyl group has to be eliminated again, this is not an economic route. Direct reaction of 2-amino-4,6-dihydroxypyrimidine with chlorodifluoromethane yields the corresponding 4,6-bis(difluoromethoxy) compound in 6.4% yield (EP-A-70,804, Example 3). Finally, special safety measures are required when handling harmful chlorodifluoromethane in order to prevent escape into the atmosphere.

It is an object of the present invention to prepare the fluoromethoxypyrimidines according to the invention in a highly selective way, without simultaneous replacement of several nuclear halogen atoms, which is, by comparison with the prior art, more straightforward, have a shorter reaction time and give better yields.

We have found that this object is achieved by an advantageous process for preparing the novel trifluoro- and chlorodifluoromethoxypyrimidines of the formula I

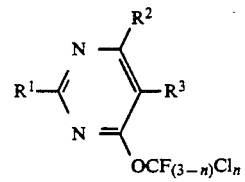

where $R^1$, $R^2$ and $R^3$ have the abovementioned meanings, by carrying out a halogen replacement on trichloromethoxyrimidines of the formula II

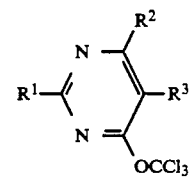

where $R^1$, $R^2$ and $R^3$ are each, independently of one another, hydrogen, halogen or $C_1$-$C_4$-haloalkyl, and $R^1$ and/or $R^2$ are also trichloromethoxy.

Suitable for the halogen replacement is antimony trifluoride in the presence or absence of a catalytic amount of an antimony(V) salt, e.g. antimony(V) chloride, or hydrogen fluoride.

The reaction between 2,4-dichloro-6-trichloromethoxypyrimidine and antimony trifluoride or hydrogen fluoride is depicted in the following diagram:

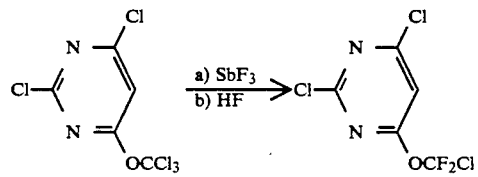

Where antimony trifluoride and the catalytic amount of antimony pentachloride or hydrogen fluoride is used, the reaction is depicted in the following diagram:

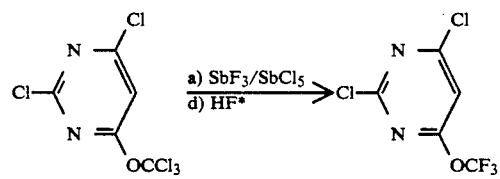

The reaction of 2-fluoro-4-trichloromethyl-6-trichloromethoxypyrimidine is depicted in the following diagram:

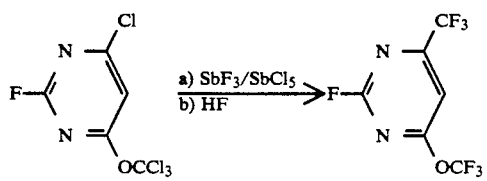

The process provides novel trifluoromethoxy- and chlorodifluoromethoxypyrimidines in high yield and purity in a straightforward and economic manner. There is no replacement of two or more nuclear chlorine atoms. In view of the prior art, all these advantageous properties are surprising.

Preferred final products I and correspondingly preferred starting materials II are those whose formulae $R^1$, $R^2$ and $R^3$ are each, independently of one another, hydrogen, fluorine, chlorine, bromine, trichloromethyl, dichlorofluoromethyl, chlorodifluoromethyl, trifluoromethyl, 1,1-dichloro-2,2,2-trifluoroethyl, 1,1,2,2,2-pentafluoroethyl or 1,1,2,2,2-pentachloroethyl and, furthermore, those final products I where $R^1$ and/or $R^2$ is also trifluoromethoxy or chlorodifluoromethoxy when $R^1$ and/or $R^2$ in the corresponding starting materials II are trichloromethoxy, and n is 0 or 1.

It is expedient to use an excess of from 1 to 200, preferably 5 to 20, mol % of antimony trifluoride per trichloromethyl equivalent. The amount of antimony(V) salt catalyst is from 1 to 20, preferably 5 to 18, mol % per trichloromethyl equivalent. The starting material II is preferably metered at from 90° to 130° C. into the mixture containing the fluorinating agent, which is then heated at from 140° to 170° C. for from 10 to about 120 minutes. Working up is then carried out by distillation.

However, the reaction can also be carried out continuously by adding the starting material II at from 140° to 170° C. over the course of from 10 to about 120 minutes and simultaneously distilling out under reduced pressure the lower boiling final product II. Traces of antimony salts which have been carried over can be removed by extraction with concentrated hydrochloric acid.

Halogen replacement can be stopped at the chlorodifluoromethoxy stage by using only small amounts, e.g. from 0.2 to 1 mol %, of antimony(V) salt catalyst, or none at all, and reducing the amount of antimony trifluoride to from 60 to 90 mol % per trichloromethyl equivalent.

In place of antimony trifluoride it is possible to use hydrogen fluoride at from 0° to 170° C., preferably 40° to 120° C. This is carried out by mixing the starting material II with an excess of from 300 to 700, preferably 350 to 400, mol % hydrogen fluoride per trichloromethyl equivalent in an autoclave and stirring for from 10 minutes to about 10 hours. In general, the reaction is complete after about 4 hours. After the pressure has been released and volatiles have been removed, working up is carried out as described.

Final products of the formula I which are preferred with a view to their further processing to herbicidal sulfonylureas are, for example, 2- or 4-trifluoromethoxypyrimidine, 4-chloro-2-trifluoromethoxypyrimidine, 2,4-bis(trifluoromethoxy)pyrimidine, 2,4-difluoro-6-trifluoromethoxypyrimidine, 6-chlorodifluoromethoxy-2,4-difluoropyrimidine, 2,4-dichloro-6-trifluoromethoxypyrimidine, 6-chlorodifluoromethoxy-2,4-dichloropyrimidine, 2-chloro-4,6-bis(trifluoromethoxy)pyrimidine, 2-chloro-4,6-bis(chlorodifluoromethoxy)pyrimidine, 4,6-dichloro-2-trifluoromethoxypyrimidine, 4,6-difluoro-2-trifluoromethoxypyrimidine, 2,4-bis(trifluoromethoxy)-6-chloropyrimidine, 2-chloro-4-trifluoromethoxy-6-trifluoromethylpyrimidine, 2-fluoro-4-trifluoromethoxy-6-trifluoromethylpyrimidine, 4-chlorodifluoromethyl-2-fluoro-6-trifluoromethylpyrimidine, 2,4-bis(trifluoromethoxy)-6-trifluoromethylpyrimidine, 4-fluoro-2-trifluoromethoxy-6-trifluoromethylpyrimidine, 2,5-dichloro-4-trifluoromethoxypyrimidine, 4,6-bis(trifluoromethoxy)-2,5-dichloropyrimidine, 2,5-difluoro-4-trifluoromethoxypyrimidine, 4,6-bis(trifluoromethoxy)-2,5-difluoropyrimidine, 2-fluoro-4-trifluoromethoxy-5-trifluoromethylpyrimidine and 2,4-bis(trifluoromethoxy)-6-trifluoromethylpyrimidine.

The trichloromethoxypyrimidines of the formula II

where $R^1$, $R^2$ and $R^3$ have the meaning mentioned in the introduction, which are required for preparing the fluorinated pyrimidines I are advantageously obtained by chlorinating methoxypyrimidines of the formula III

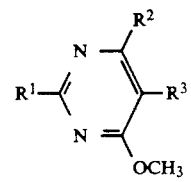

where $R^1$, $R^2$ and $R^3$ are each, independently of one another, hydrogen, halogen or $C_1$–$C_4$-haloalkyl, and $R^1$ and/or $R^2$ are also methoxy.

The success of the process is surprising because nuclear halogenation and side reactions would have been expected to a greater extent based on the fact that methoxy is a good electron donor. A marked tendency to halogenation in the 5-position is evident from the chlorination of 6-chlorouracil in water at 80° C. to give 4,5-dichloro-2,6-dihydroxypyrimidine in 60% yield (Isr. J. Chem. 6 (1968) 603).

The reaction of 2,4-dichloro-6-methoxypyrimidine with chlorine as chlorinating agent is depicted by the following diagram:

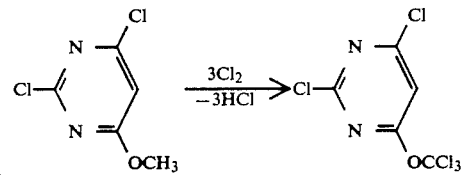

The process provides novel trichloromethoxypyrimidines in high yield and purity in a straightforward and economic manner without simultaneous formation of 5-chlorinated by-products. In view of the prior art, all these advantageous properties are surprising.

Preferred intermediates II and accordingly preferred starting materials III are those in whose formulae $R^1$, $R^2$ and $R^3$ are each, independently of one another, hydrogen, fluorine, chlorine, bromine, trichloromethyl, dichlorofluoromethyl, chlorodifluoromethyl, trifluoromethyl, 1,1-dichloro-2,2,2-trifluoroethyl, 1,1,2,2,2-pentafluoroethyl or 1,1,2,2,2-pentachloroethyl, and, furthermore, those products II where $R^1$ and/or $R^2$ are also trichloromethoxy when $R^1$ and/or $R^2$ in the corresponding starting materials are methoxy.

Suitable chlorinating agents are elemental chlorine and substances which release chlorine such as sulfuryl chloride or phosphorus pentachloride. It is also possible to generate chlorine in situ by oxidizing hydrochloric acid, for example with pyrolusite or by anodic chlorination.

The chlorination can be carried out in the presence of an inert solvent, for example a chlorohydrocarbon such as chloroform, tetrachloromethane, chlorobenzene, 1,2- or 1,3- or 1,4-dichlorobenzene, a nitrile such as acetonitrile or propionitrile, a nitro compound such as nitrobenzene, a carboxylic acid such as acetic or propionic acid, an anhydride such as acetic anhydride, an acid chloride such as chloroacetyl chloride, α-chloropropionyl chloride or α,α-dichloropropionyl chloride, an inorganic acid halide such as phosphorus trichloride or phosphorus oxychloride or, preferably, without solvent in the melt of the starting material III.

A radical initiator can be used to increase the reaction rate; suitable for this is irradiation with light, preferably UV light, or addition of α,α,-azoisobutyronitrile, expediently in an amount of from 0.2 to 7 mol % based on the starting material III. The reaction rate can also be increased by addition of a catalyst; suitable for this is phosphorus pentachloride, expediently in an amount of from 0.5 to 7 mol % based on the starting material III. In this case, the starting material III is mixed with the catalyst and then the chlorination is started. In place of phosphorus pentachloride, it is also possible to add components which form it under the reaction conditions, e.g. phosphorus trichloride or yellow phosphorus, and then to start with the chlorination.

Starting material III can be reacted with chlorine in approximately stoichiometric amount or, preferably, in excess, advantageously with from 3.1 to 11, in particular 3.3 to 5, moles of chlorine per methoxy equivalent in the starting material III. The reaction can be carried out at from 60° to 180° C., advantageously from 100° to 150° C., under atmospheric or superatmospheric pressure continuously or batchwise.

When chlorination is carried out under 1 bar it is expedient to employ from 3.3 to 5 moles of chlorine gas based on one methoxy equivalent in the starting material III which corresponds to a chlorine conversion of from 91 to 60%. It is possible, by suitable measures, e.g. by use of moderate superatmospheric pressure, expediently from 1 to 10 bar, or by use of a bubble column, to increase the chlorine conversion. It is advantageous to maximize the time during which the chlorine gas is in contact with the organic phase by, for example, vigorously stirring the latter or forcing the chlorine gas to pass through a thick layer of the organic phase.

The reaction time is generally from about 0.5 to 12 hours.

The procedure in a preferred embodiment of the process is to pass the required amount of chlorine gas over the course of from 0.5 to 12 hours, preferably 1 to 10 hours, into the vigorously stirred liquid starting material III, starting at from 60° to 80° C. and increasing the temperature continuously, possibly by utilizing the exothermic nature of the reaction, to from 100° to 150° C. at the end of the reaction. In the case of large batches, the exothermic nature of the reaction must be taken into account by applying external cooling or by suitable metering in of the chlorine; when the reaction subsides the cooling bath is removed and the mixture may then be heated.

The final products are worked up and isolated in a conventional manner. For example, residual hydrogen chloride, chlorine or catalyst can be driven out of the hot organic phase using an inert gas; this results in a high yield of a reasonably pure crude product. It can be further purified by distillation or chromatography or else employed immediately for further reactions.

Examples of preferred compounds of the formula II are 2- and 4-trichloromethoxypyrimidine, 4-chloro-2-trichloromethoxypyrimidine, 2,4-bis(trichloromethoxy)pyrimidine, 2,4,6-tris(trichloromethoxy)pyrimidine, 2,4-difluoro-6-trichloromethoxypyrimidine, 2-fluoro-4,6-bis(trichloromethoxy)pyrimidine, 4,6-difluoro-2-trichloromethoxypyrimidine, 2,4-bis(trichloromethoxy)-6-fluoropyrimidine, 2,4-dichloro-6-trichloromethoxypyrimidine, 2-chloro-4,6-bis(trichloromethoxy)pyrimidine, 4,6-dichloro-2-trichloromethoxypyrimidine, 2,4-bis(trichloromethoxy)- 6-chloropyrimidine, 2-Chloro-4-trichloromethoxy-6-trichloromethylpyrimidine, 2-chloro-4-trichloromethoxy-6-trifluoromethylpyrimidine, 2,4-bis(trichloromethoxy)-6-trichloromethylpyrimidine, 2,4-bis(trichloromethoxy)-6-trifluoromethylpyrimidine, 2-fluoro-4-trichloromethoxy-6-trichloromethylpyrimidine, 2-fluoro-4-trichloromethoxy-6-trifluoromethylpyrimidine, 4-fluoro-2-trichloromethoxy-6-trichloromethylpyrimidine, 4-fluoro-2-trichloromethoxy-6-trifluoromethylpyrimidine, 2,5-dichloro-4-trichloromethoxypyrimidine, 4,6-bis(trichloromethoxy)-2,5-dichloropyrimidine, 2,5-difluoro-4-trichloromethoxypyrimidine, 4,6-bis(trichloromethoxy)-2,5-difluoropyrimidine, 2-chloro-4-trichloromethoxy-5-trifluoromethylpyrimidine, 2-fluoro-4-trichloromethoxy-5-trifluoromethylpyrimidine, 2-chloro-4-trichloromethoxy-6-trifluoromethylpyrimidine, 2-fluoro-4-trichloromethoxy-6-trifluoromethylpyrimidine, 4-chloro-2-trichloromethoxy-6-trifluoromethylpyrimidine, 2,4-bis(trichloromethoxy)-6-trifluoromethylpyrimidine and 4-chloro-2-trifluoromethyl-6-trichloromethoxypyrimidine.

The novel trichloromethoxypyrimidines II and the novel trifluoro- and chlorodifluoromethoxypyrimidines I are valuable intermediates for preparing drugs, dyes and crop protection agents.

For example, the compounds I 2,4-dichloro- or 2,4-difluoro-6-trifluoromethoxypyrimidine can be converted with ammonia and methanol into the corresponding 2-amino-6-methoxy-4-trifluoromethoxypyrimidine which reacts with 2-carbomethoxybenzenesulfonyl isocyanate to give-herbicidal sulfonylureas.

Subsequent reactions of this type are described in Applications P .. .. ... (O.Z. 0050/41451) and P .. .. ... (O.Z. 0050/41452) of the same date.

EXAMPLES

Examples 1

I Examples of the Preparation of the Precursors

Example I.1

2-Chloro-4-trichloromethoxy-6-trichloromethylpyrimidine a) 2-Chloro-4-methoxy-6-trichloromethylpyrimidine 293.1 g (1.692 mol) of 30% strength sodium methylate solution were added over the course of 1½ hours to a stirred solution of 434 g (1.692 mol) of 2,6-dichloro-4-trichloromethylpyrimidine in 1 l of 1,2-dichloroethane at 0° to 5° C. The mixture was then stirred at 0° to 5° C. for 1 hour and at 25° C. for 12 hours and then extracted ×4 with water and ×3 with saturated brine. Drying over magnesium sulfate and concentration resulted in 423 g (95% of theory) of the title compound as an almost colorless oil.

¹H-NMR (CDCl₃) (ppm) OCH₃ (s/3H) 4.1; CH (s/1H) 7.25.

b) 2-Chloro-4-trichloromethoxy-6-trichloromethylpyrimidine

Chlorine was passed into a mixture of 210 g (0.802 mol) of a) and 260 mg (0.0016 mol) of α,α'-azoisobutyronitrile, initially at 110° C., with UV irradiation and monitoring of the progress of the reaction by gas chromatography. The temperature stabilized at 140° C. even after removal of the heating bath. After the reaction had subsided a total of 341 g (4.8 mol) of chlorine was passed in at 120° C. over the course of 5½ hours. The reaction mixture was cooled to 40° C. and 70 ml of n-pentane were stirred in. The precipitate was filtered off with-suction, washed with petroleum ether and dried, resulting in 163 g (55% of theory) of the title compound of melting point 67°–69° C.

The gas chromatogram of the filtrate (113.8 g) showed that it was composed of 83% title compound, 4% 2-chloro-4-dichloromethoxy-6-trichloromethylpyrimidine and 9% 2,4-dichloro-6-trichloromethylpyrimidine. The total yield of the title compound was 87.6% of theory.

Example I.2

2,4-Difluoro-6-trichloromethoxypyrimidine a) 2,4-Difluoro-6-methoxypyrimidine (Preparation by the process of the older German Patent Application P 39 00 471.6 of Jan. 10, 1989 (O.Z. 0050/40474)).

335.8 g (1.865 mol) of 30% strength sodium methylate (in methanol) were added to a mixture of 250 g (1.865 mol) of 2,4,6-trifluoropyrimidine and 1.4 1 of methanol at −20° C. over the course of 45 minutes, and the mixture was stirred at this temperature for a further 30 minutes. It was then allowed to warm to 25° C. and concentrated to about 1/5 of its volume.

The resulting mixture was partitioned between diethyl ether and water, and then the organic phase was dried over magnesium sulfate and concentrated. Distillation resulted in 141.6 g (52% of theory) of the title compound of boiling point 144°–145° C.

Distillation of the residue with a Normag head resulted in 114.4 g (42% of theory) of 4,6-difluoro-2-methoxypyrimidine of boiling point 157°–161° C.

b) 2,4-Difluoro-6-trichloromethoxypyrimidine 210 g (2.96 mol) of chlorine were passed over the course of 2½ hours into 123 g (0.843 mol) of 2,4-difluoro-6-methoxypyrimidine which was stirred at 130° C. and exposed to UV irradiation, with monitoring of the progress of the reaction by gas chromatography. The reaction mixture was distilled through a 10 cm Vigreux column under reduced pressure, resulting in 190.2 g (90.5% of theory) of the title compound of boiling point 40°–43° C./0.2 mbar.

Example I.3

2,4-Dichloro-6-trichloromethoxypyrimidine 303 g (4.27 mol) of chlorine were passed into a mixture of 209 g (1.168 mol) of 2,6-dichloro-4-methoxypyrimidine and 2 g (0.012 mol) of α,α'-azoisobutyronitrile while stirring at 80° C. for hour, at 100° C. for hour, at 120° C. for 3 hours and at 150° C. for 3 hours and subjecting to UV irradiation, with monitoring of the progress of the reaction by gas chromatography. The reaction mixture was then distilled under reduced pressure. 241.3 g (73% of theory) of the title compound of boiling point 87°–88° C./0.4 mbar, melting point 55°–56° C. were obtained.

II Conversion to the Final Products I

Example II.1

2,4-Difluoro-6-trifluoromethoxypyrimidine 49.9 g (0.2 mol) of 2,4-difluoro-6-trichloromethoxypyrimidine were added over the course of 15 minutes to a stirred mixture of 39.3 g (0.22 mol) of antimony trifluoride and 9.38 g (0.031 mol) of antimony pentachloride at 100° C. The bath temperature was increased from 100° to 150° C. over the course of 25 minutes, and the mixture was then stirred for 30 minutes, reflux taking place at from 120° to 125° C. Subsequent distillation resulted in 37.1 g (92.7% of theory) of the title compound of boiling point 125°–127° C.

Example II.2

6-Chlorodifluoromethoxy-2,4-difluoropyrimidine 93 g (0.373 mol) of 2,4-difluoro-6-trichloromethoxypyrimidine were added over the course of 10 minutes to a stirred mixture of 44.5 g (0.249 mol) of antimony trifluoride and 0.94 g (0.0031 mol) of antimony pentachloride at 100° C. The bath temperature was raised from 100° to 175° C. over the course of 25 minutes, reflux taking place at 145° C. After stirring for 1½ hours, the reaction product was distilled out at 146°–150° C. The distillate was dissolved in methylene chloride, and the solution was extracted with 6 N hydrochloric acid and dried over magnesium sulfate. Concentration under reduced pressure resulted in a residue of the title compound in a yield of 63.7 g =78.8% of theory.

Example II.3

2-Fluoro-4-trifluoromethoxy-6-trifluoromethylpyrimidine 80 g (0.219 mol) of 2-chloro-4-trichloromethyl-6-trichloromethoxypyrimidine were added over the course of 5 minutes to a stirred mixture of 93.9 g (0.525 mol) of antimony trifluoride and 18.7 g (0.0627 mol) of antimony pentachloride at 100°. The bath temperature was raised to 140° C. over the course of 10 minutes, and the mixture was then stirred for 1 hour, during which it refluxed vigorously. The reaction product was distilled at 135°–140° C. and, towards the end, at 95° C./50 mbar. The distillate was taken up in methylene chloride, and the solution was extracted with 6 N hydrochloric acid and dried over magnesium sulfate. Concentration under reduced pressure resulted in the title compound in a yield of 35.9 g (65.5% of theory).

Example II.4

2,4-Dichloro-6-trifluoromethoxypyrimidine 115 g (0.407 mol) of 2,4-dichloro-6-trichloromethoxypyrimidine were added over the course of 5 minutes to a stirred mixture of 80 g (0.447 mol) of antimony trifluoride and 18.77 g (0.0627 mol) of antimony pentachloride at 100° C., during which the reaction temperature rose to 140° C. The mixture was then stirred at 150° C. for 45 minutes. The title compound distilled at 128° C. under 210 mbar; remaining volatiles were driven over at 110° C./ 22 mbar. The distillate was dissolved in methylene chloride, and the solution was extracted with 6 N hydrochloric acid and dried over magnesium sulfate. Concentration under reduced pressure resulted in the title compound in a yield of 80 g (84.4% of theory) of colorless oil of $n_D^{25}=1.4604$.

III Conversion of Compounds I into Herbicidal Sulfonylureas

Example III.1

2-Amino-4-chlorodifluoromethoxy-6-fluoropyrimidine 9.8 g (0.578 mol) of gaseous ammonia were passed over the course of one hour into a stirred mixture of 62.5 g (0.289 mol) of 2,4-difluoro-6-chlorodifluoromethoxypyrimidine and 300 ml of tetrahydrofuran at −75 to −70° C. The mixture was stirred at −70° C. for one hour and then warmed to room temperature. The precipitate was filtered off with suction and partitioned between ethyl acetate and water, and the organic phase was dried over magnesium sulfate, filtered and concentrated. The residue was dissolved in ethyl acetate, chromatographed on silica gel with 5:1 petroleum ether/ether and concentrated. 46.5 g (75.3% of theory) of the title compound were obtained as colorless crystals of melting point 77°–80° C.

Example III.2

2-Amino-4-fluoro-6-trifluoromethoxypyrimidine 8.7 g (0.51 mol) of gaseous ammonia were passed over the course of 1 hour into a stirred mixture of 51 g (0.255 mol) of 2,4-difluoro-6-trifluoromethoxypyrimidine and 200 ml of diethyl ether at −75° to −70° C. The mixture was stirred at −70° C. for 1½ hours and at room temperature for 1 hour and then concentrated under reduced pressure. The residue was taken up in methylene chloride and the organic phase was extracted with water, dried, concentrated and chromatographed on silica gel with 8:1 petroleum ether/ether, resulting in 38.1 g (75.6% of theory) of the title compound as colorless crystals of melting point 86°–89° C.

Example III.3

2-Amino-4-chloro-6-trifluoromethoxypyrimidine 4.3 g (0.25 mol) of gaseous ammonia were passed over the course of 45 minutes into a stirred mixture of 23.3 g (0.1 mol) of 2,4-dichloro-6-trifluoromethoxypyrimidine and 150 ml of methyl tert.-butyl ether at −50° to −45° C. The mixture was stirred at −50° C. for 30 minutes, at −30° C. for 1 hour and at 25° C. for 1 hour. The precipitate was filtered off with suction, washed with water and dried, resulting in 5.4 g (33.1% of theory) of 4-amino-2,4-dichloropyrimidine of melting point 270°–272° C. as by-product. The filtrate was washed with water, dried and concentrated under reduced pressure, and the residue was chromatographed with 5:1 petroleum ether/ether, the initial fractions yielding 3 g (12.8% of theory) of starting material as a colorless oil, and subsequent fractions containing 9 g (42% of theory) of the title compound as colorless crystals of melting point 55°–56° C. Conversion was 48.3%.

Example III.4

4-Chlorodifluoromethoxy-6-fluoro-2-methylaminopyrimidine 20.3 g (0.0938 mol) of 4-chlorodifluoromethoxy-2,6-difluoropyrimidine were introduced into 150 ml of tetrahydrofuran and, while stirring at −70° to −60° C., 5.8 g (0.188 mol) of gaseous methylamine were added over the course of 30 minutes. The mixture was stirred for 1 hour each at −70° C., 0° C. and 25° C. and concentrated under reduced pressure. The residue was stirred with water, the mixture was extracted 2×with ethyl acetate, and the extract was dried over magnesium sulfate. The residue from concentration under reduced pressure was chromatographed on silica gel with 5:1 petroleum ether/ether. The first fractions contained the title compound of melting point 57°–61° C. in a yield of 12.5 g (58.5%).

Example III.5

2-Amino-4-trifluoromethoxy-6-trifluoromethylpyrimidine 4.7 g (0.278 mol) of gaseous ammonia were passed over the course of 1 hour into a stirred mixture of 38.0 g (0.147 mol) of 2-fluoro(chloro)-4-trifluoromethoxy-6-trifluoromethylpyrimidine and 150 ml of diethyl ether at −75° to −70° C. The mixture was stirred for 2 hours each at −75° and at 25° C. The precipitate was filtered off with suction, and the organic phase was extracted with water, dried and evaporated. Chromatography on silica gel with methyl tert.-butyl ether yielded 20.4 g (56.1% of theory) of the title compound of melting point 47°–49° C.

Example III.6

2-Amino-4-methoxy-6-trifluoromethoxypyrimidine 2.7 g (0.015 mol) of 30% strength sodium methylate were added over the course of 15 minutes to 2.95 g (0.015 mol) of 2-amino-4-fluoro-6-trifluoromethoxypyrimidine in 50 ml of methanol while stirring at −5° to 0° C. The reaction mixture was stirred at 0° C. for 1 hour, warmed to 25° C. and then concentrated under reduced pressure, stirred with water and extracted 2×with methylene chloride. Drying and concentrating under reduced pressure resulted in 3.1 g (98% of theory) of the title compound of $n_D^{25}=1.4770$.

Example III.7

2-Amino-4-chlorodifluoromethoxy-6-methoxypyrimidine 26.1 g (0.145 mol) of 30% strength sodium methylate were added over the course of 15 minutes to 31.0 g (0.145 mol) of 2-amino-4-chlorodifluoromethoxy-6-fluoropyrimidine in 300 ml of methanol while stirring at −10° to 0° C. The reaction mixture was stirred at 0° C. for 30 minutes and at 25° C. for 1 hour and then concentrated under reduced pressure and worked up as above. 31.6 g (96.6% of theory) of the title compound were obtained as a colorless oil with $n_D^{22}=1.5039$.

Example III.8

4-Chlorodifluoromethoxy-2-methylamino-6-methoxypyrimidine 4.7 g (0.026 mol) of 30% strength sodium methylate were added over the course of 10 minutes to 6.0 g (0.0263 mol) of 4-chlorodifluoromethoxy-6-fluoro-2-methylaminopyrimidine in 100 ml of methanol while stirring st 0° C. The mixture was stirred at 0° C. and at 25° C. for 1 hour each and worked up as usual, resulting in 6.3 g (100% of theory) of the title compound of melting point 49°–53° C.

Example III.9

4-Chlorodifluoromethoxy-6-dimethylamino-2-methylaminopyrimidine 1.9 g (0.0417 mol) of gaseous dimethylamine were passed over the course of 10 minutes into a stirred mixture of 8.9 g (0.0417 mol) of 2-amino-4-chlorodifluoromethoxy-6-fluoropyrimidine and 100 ml of tetrahydrofuran at 0° C. The mixture was stirred at 0° C. for 1 hour and at 25° C. for 2 hours and worked up as usual, resulting in 9.7 g (97.5% of theory) of the title compound of melting point 127°–130° C.

Example III.10

Methyl 2-(4-fluoro-6-trifluoromethoxy-2-pyrimidinylaminocarbonylaminosulfonyl)benzoate 3.6 g (0.015 mol) of 2-methoxycarbonylbenzenesulfonyl isocyanate in 15 ml of 1,2-dichloroethane were added over the course of 15 minutes to a stirred mixture of 2.95 g (0.015 mol) of 2-amino-4-fluoro-6-trifluoromethoxypyrimidine and 100 ml of 1,2-dichloroethane at 25° C., and the mixture was stirred at 25° C. for 12 hours. The solution was concentrated under reduced pressure, and the residue was stirred with 1:1 ether/petroleum ether. Filtration with suction and drying yielded 4.8 g (73.3% of theory) of the title compound of melting point 157°–161° C.

Example III.11

Ethyl 2-(4-chloro-6-trifluoromethoxy-2-pyrimidinylaminocarbonylaminosulfonyl)benzoate 2.55 g (0.01 mol) of 2-ethoxycarbonylbenzene isocyanate in 10 ml of methylene chloride were added over the course of 10 minutes to a stirred mixture of 2.1 g (0.01 mol) of 2-amino-4-chloro-6-trifluoromethoxypyrimidine and 100 ml of methylene chloride at 25° C. The mixture was stirred at 25° C. for 12 hours and filtered with suction to remove a few insolubles. Concentration of the filtrate under reduced pressure, stirring of the residue with 1:1 ether/petroleum ether, filtration with suction and drying yielded 4.0 g (85.4% of theory) of the title compound of melting point 148°–151° C.

Example III.12

Methyl 2-(4-methoxy-6-trifluoromethoxy-2-pyrimidinylaminocarbonylaminosulfonyl)benzoate 4.8 g (0.02 mol) of 2-methoxycarbonylbenzenesulfonyl isocyanate in 10 ml of acetonitrile were added over the course of 15 minutes to a stirred mixture of 4.1 g (0.02 mol) of 2-amino-4-methoxy-6-trifluoromethoxypyrimidine and 100 ml of acetonitrile at 25° C., and the mixture was then stirred for 12 hours. The precipitate was removed (2.4 g of melting point 141°–143° C.) and then the filtrate was concentrated under reduced pressure and stirred with ether/petroleum ether, and the solid was filtered off with suction and dried. A further 4.3 g of the title compound of melting point 141°–143° C. were obtained. The total yield was 6.7 g (74.4% of theory).

Example III.13

Sodium salt of methyl 2-(4-methoxy-6-trifluoromethoxy-2-pyrimidinylaminocarbonylaminosulfonyl)benzoate 2.4 g (0.053 mol) of methyl 2-(4-methoxy-6-trifluoromethoxy-2-pyrimidinylaminocarbonylaminosulfonyl)benzoate were dissolved in 50 ml of methanol and, at 25° C., 1.0 g (0.053 mol) of 30% strength sodium methylate solution in methanol was added, and the mixture was stirred for 10 minutes. Removal of the solvent by distillation under reduced pressure yielded 2.5 g (100% of theory) of the title compound of melting point 175° C.

We claim:

1. A substituted trifluoro- or chlorodifluoromethoxypyrimidine of the formula I

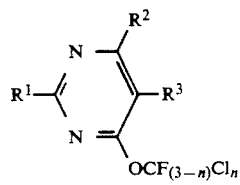

where $R^1$, $R^2$ and $R^3$ are each, independently of one another, hydrogen, halogen, or $C_1$–$C_4$-haloalkyl, and $R^1$ and/or $R^2$ is also trifluoromethoxy or chlorodifluoromethoxy, and n is 0 or 1.

2. 2,4-Difluoro-6-trifluoromethoxypyrimidine.
3. 6-Chlorodifluoromethoxy-2,4-difluoropyrimidine.
4. 2-Fluoro-4-trifluoromethoxy-6-trifluoromethylpyrimidine.
5. 2,4-Dichloro-6-trifluoromethoxypyrimidine.
6. A substituted trichloromethoxypyrimidine of the formula II

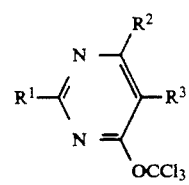

where $R^1$, $R^2$ and $R^3$ are each, independently of one another, hydrogen, halogen or $C_1$–$C_4$-haloalkyl, and $R^1$ and/or $R^2$ is also trichloromethoxy.

7. 2,4-Dichloro-6-trichloromethoxypyrimidine.
8. 2,4-Difluoro-6-trichloromethoxypyrimidine.
9. 2-Chloro-4-trichloromethoxy-6-trichloromethylpyrimidine.

* * * * *